United States Patent [19]

Choudhury

[11] 4,140,126
[45] Feb. 20, 1979

[54] METHOD FOR PERFORMING ANEURYSM REPAIR

[76] Inventor: M. Hasan Choudhury, 510 E. Cottonwood, Coldwater, Kans. 67029

[21] Appl. No.: 770,100

[22] Filed: Feb. 18, 1977

[51] Int. Cl.$^2$ .................... A61B 17/00; A61B 17/12
[52] U.S. Cl. .................................. 128/325; 128/348; 3/1.4; 138/97; 138/98
[58] Field of Search ............... 128/334 R, 1 R, 334 C, 128/303 R, 349 B, 348, 325; 3/1.4, 1; 138/97, 98; 264/36

[56] References Cited

U.S. PATENT DOCUMENTS

| 2,977,994 | 4/1961 | Xenis ...................................... 138/97 |
| 3,334,629 | 8/1967 | Cohn ....................................... 128/325 |
| 3,369,549 | 2/1968 | Armao ................................. 128/303.1 |
| 3,834,394 | 9/1974 | Hunter et al. ......................... 128/348 |
| 3,903,893 | 9/1975 | Scheer ................................... 128/325 |
| 3,938,528 | 2/1976 | Bucalo ............................. 128/334 C |
| 3,991,767 | 11/1976 | Miller, Jr. et al. .................... 128/348 |
| 4,056,854 | 11/1977 | Boretos et al. ....................... 128/1 R |

FOREIGN PATENT DOCUMENTS

| 1128232 | 2/1959 | Fed. Rep. of Germany ............. 138/97 |
| 1505607 | 11/1967 | France ................................. 128/349 B |
| 2302755 | 10/1976 | France .................................... 128/348 |

OTHER PUBLICATIONS

The Bulletin of the Dow Corning Center for Aid to Medical Research, vol. 2, No. 3, Jul. 1960, Luessenhop, A. J., "Intra-Arterial Instrumentation for neurosurgery".
Hunter, J. A., Experimental Balloon Obstruction of the Inferior Vena Cava, In Annal of Surgery, Feb. 1970, pp. 315-320.

Primary Examiner—Robert W. Michell
Assistant Examiner—Arthur S. Rose
Attorney, Agent, or Firm—Lowe, Kokjer, Kircher, Wharton & Bowman

[57] ABSTRACT

A method and article for performing an aneurysm repair is the subject of the present invention. A prosthetic graft is utilized to replace the damaged segment of the blood vessel. The graft is characterized by being movable from a collapsed formation of a diameter less than the diameter of the vessel to an open formation of a diameter approximately equal to that of the vessel. A plurality of radially spaced anchoring pins are located adjacent each end of the graft and provide means for securing the graft to the wall of the healthy vessel, on opposite sides of the aneurysm. Once in place, hemodynamic pressure will assure a continued fluid tight seal between the graft and the healthy vessel wall tissue. The prosthetic graft may be used without the need for major surgery by securing it to a catheter and inserting the catheter at a distal location from the aneurysm. The catheter with the prosthetic graft attached is moved through the vessel, utilizing fluoroscopic and X-ray data, to the area of the aneurysm. When in the proper location, the graft is moved, through remote control, to the open formation where the anchoring pins secure it to the vessel wall. The catheter may then be withdrawn as is the remote control operative linkage.

3 Claims, 4 Drawing Figures

U.S. Patent    Feb. 20, 1979    4,140,126
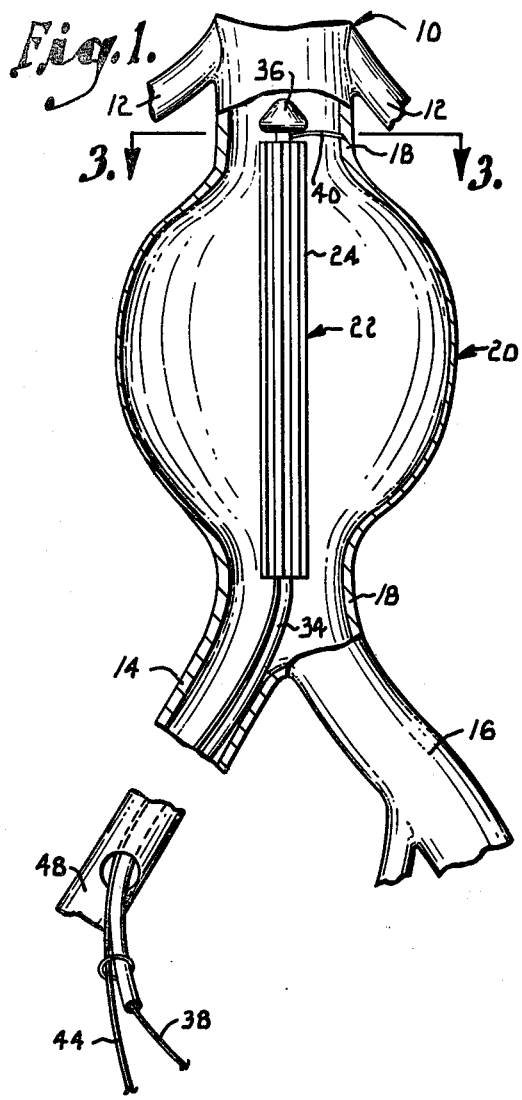
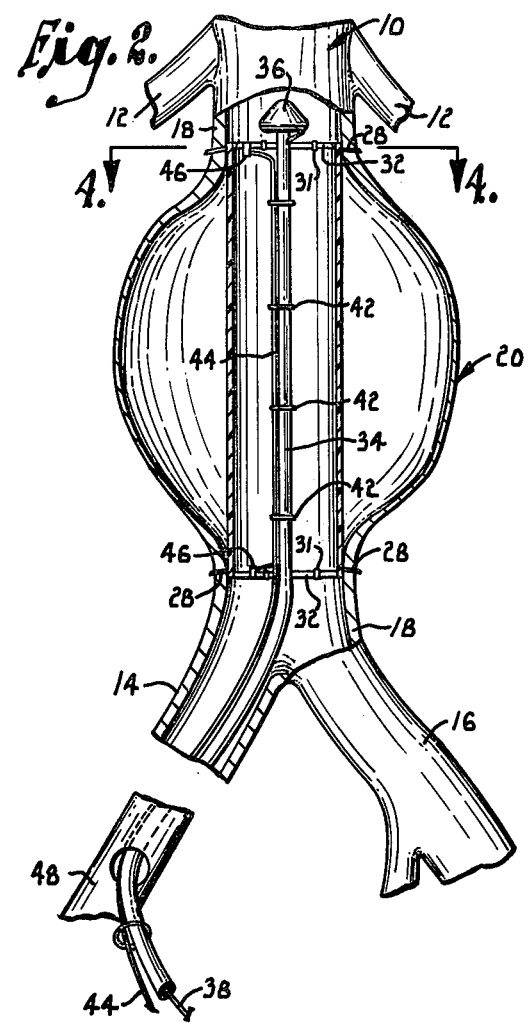
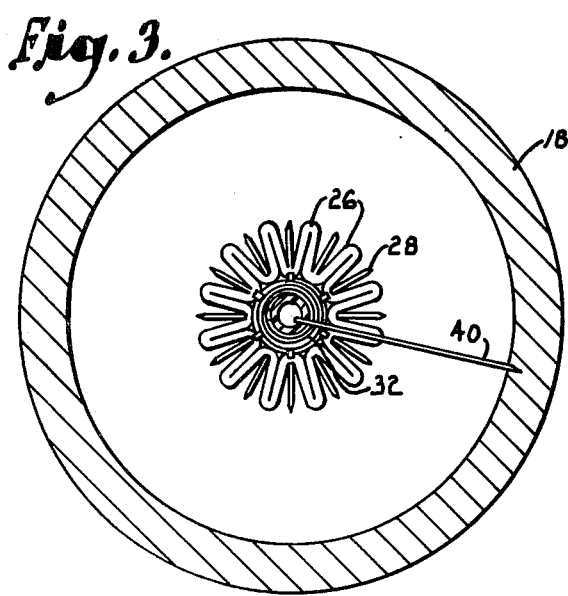
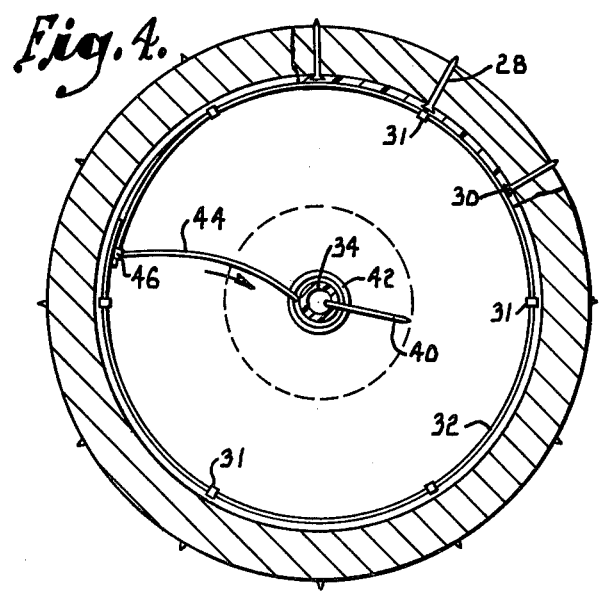

METHOD FOR PERFORMING ANEURYSM REPAIR

This invention relates generally to a cardiovascular surgical technique and, more particularly, to a method and article for performing an aneurysmectomy.

Excisional aneurysm surgery has been performed for approximately 25 years. The accepted surgical technique of excising the aneurysm and replacing the void with a prosthetic graft has been continuously improved over the years. Still, the mortality rate for patients undergoing the surgery remains relatively high. One reason for the high mortality rate is that the operation constitutes a major surgical undertaking, making it highly elective in patients with severe coronary or cerebral arteriosclerosis, severe restrictive pulmonary disease, significant renal disease or other complicating factors.

Another major disadvantage of presently accepted excisional aneurysm surgical techniques is that because of the severe nature of the operation, it can be performed only in relatively sophisticated medical centers having the capacity to perform major cardiovascular surgery. In cases where the diagnosis is not made until the prognosis for a rupture may be critical, fatalities have been known to occur because of insufficient time to transfer the patient to a major medical center where corrective surgery could be performed.

It is therefore the primary object of the present invention to provide a method and article for performing an aneurysm repair which does not require major surgery and may therefore be used on higher risk patients than conventional excisional aneurysm surgery.

As a corollary to the above object, a primary aim of my invention is to provide a method and article for performing an aneruysm repair at medical centers which are not equipped for major cardiovascular surgery, thereby reducing the time between diagnosis and corrective surgery.

Another important object of this invention is to provide a method and article for performing an aneurysm repair which may be utilized to stabilize a critical patient for a period of time until conventional excisional aneurysm surgery may be performed if it is determined this is desirable.

An objective of the invention is also to provide a method and article for performing an aneurysm repair which may be utilized in conjunction with existing angiographic catheters which will serve as carriers to move a prosthetic graft to the area of the aneurysm while also assisting in providing conventional X-ray and fluoroscopic data.

Another very important aim of my invention is to provide a method and article for performing an aneurysm repair which will result in a more favorable mortality rate as a result of the less severe surgical technique.

Other objects of the invention will be clear or become apparent from the following description and claims when read in light of the accompanying drawing wherein:

FIG. 1 is a greatly enlarged top plan view, this showing major portions in cross-section, of an aneurysm in the abdominal aorta and with the article of the present invention shown in proximity thereto;

FIG. 2 is a view substantially similar to FIG. 1 but with the prosthetic graft of the present invention disposed in its open formation wherein it effects resectioning of the blood vessel;

FIG. 3 is a horizontal cross-sectional view taken along line 3—3 of FIG. 1;

FIG. 4 is a horizontal cross-sectional view taken along line 4—4 of FIG. 2.

Referring initially to FIG. 1, the abdominal aorta is indicated generally by the numeral 10 although it will be appreciated that the drawing is intended to be illustrative and is not necessarily a scale drawing. Renal arteries 12 extend from aorta 10 and the latter divides into the common iliac arteries 14 and 16 at its lowermost end. Aorta 10 is a major blood carrying vessel of the body and is characterized throughout most of its length by healthy tissue 18 which presents the artery wall. A damaged segment of aorta 10 is indicated generally by the numeral 20 where a large aneurysm has formed. Manifestly, if the aneurysm is not repaired it is likely that in time it will rupture, causing a fatal hemorrhage in a manner of minutes.

The present invention comprises a prosthetic graft designated generally by the numeral 22 for repairing the damaged aorta segment. Graft 22 is preferably constructed from a material such as Dacron which is known to be sufficiently biologically innert to permit safe insertion inside the human body. Graft 22 comprises an elongated tube 24 which is moveable into a collapsed formation, best illustrated in FIG. 3, wherein a plurality of folds 26 which extend longitudinally for the length of the tube are interspaced with a plurality of radially spaced anchoring pins 28. Pins 28 may be constructed of rigid plastic, stainless steel, or other biologically acceptable material and are held in place by an integral plate 30 which, for the sake of clarity has been omitted from FIG. 3 but is shown in broken lines in FIG. 4. Plate 30 is in turn imbedded in the tubular material 24. A second identical set of anchoring pins 28 is located at the lowermost end of tube 24 and are illustrated in FIG. 2.

The tube 24 is mounted in the collapsed formation shown in FIGS. 1 and 3 on upper and lower convoluted expansions rings 32. Slip rings 31 which pass through the tube material 24 and around ring 32 permit the latter to "unwind" while still holding the tube in place.

Tube 24 is preferably collapsed around a carrier line which may be a modified catheter tube 34. Catheter tube 34 is fitted with a head 36 at its end so as to facilitate movement of the tube with graft 22 there-around through the blood vessel. It is to be understood that one or more openings (not shown) may be provided in head 36 so as to permit the introduction of dyes or other fluids through the catheter. Disposed inside of catheter 34 is a wire 38 which leads to a positioning hook 40. Coupled with catheter 34 by a plurality of slip rings 42 is an expansion lead wire 44. Wire 44 is coupled with expansion rings 32 by sleeve type slip couplings 46.

In utilizing the device of the present invention to repair a damaged segment of a blood vessel, appropriate diagnosis is first made to determine the location of the aneurysm or other defect. It will be appreciated that while the invention is described herein with reference to an aneurysm in the abdominal aorta, this is done only for purposes of illustration and the invention will also have applicability to aneurysms in other locations. The abdominal aorta is, however, an area of frequent occurrence of aneurysms.

Graft 22 is collapsed around catheter 34 in the manner illustrated in FIGS. 1 and 3, outside of the body. It will be appreciated that tube 24 may be constructed of a material which will hold the collapsed formation until it is desired to expand the tube and, if necessary, optional retention means (not shown) which will dissolve in a relatively short period of time may be utilized to help retain the collapsed formation. That is, any one of a number of materials which are readily known to those skilled in the art and which will dissolve in the aqueous base blood flowing through the body may be used as ties to facilitate holding the tube 24 in the collapsed formation. The material may be designed to be easily broken upon exerting an expansion force if it has not become completely dissolved at the time expansion is desired to take place. It will also be appreciated that before catheter 34 with graft 22 in place is inserted into the body, positioning hook 40 is withdrawn to a location beneath head 36 as is illustrated in FIG. 2.

An incision is made at a location distal from the aneurysm, preferably in the femoral artery 48 in the case of an aneurysm in the lower end of the abdominal aorta. If the femoral artery is closed or if location of the aneurysm dictates, insertion of the catheter may also take place through one of the carotid or subclavian arteries. The catheter is guided with the help of X-ray or fluoroscopic data to the location of the aneurysm where the positioning hook 40 is moved outwardly by pushing on lead wire 38. It will be appreciated that wire 38 is relatively flexible material which is capable of making a 90 degree bend as it pushes against head 36. Thus, positioning hook 40 will extend into the position illustrated in FIG. 1 where it may be moved to pierce artery wall 18 and hold both the catheter and graft 22 temporarily in place. This permits final confirmation of the proper position of the graft through X-ray and fluoroscopic data before expansion occurs. If the position is not what is desired, positioning hook 40 may be withdrawn to free catheter 34 and allow repositioning prior to expansion of the graft.

When the proper position for graft 22 is determined, wire 44 is pushed against the convoluted expansion rings 32 thereby causing the convolutions to move apart and form a singular ring of larger diameter. Manifestly, slip rings 31 permit the expansion ring 32 to move relative to the folded expansion tube 24. As tube 24 expands, anchoring pins 28 will pierce the healthy artery wall 18 on opposite sides of aneurysm 20. Once in place, the hemodynamic pressure of blood passing through graft 22 will facilitate maintenance of its expanded formation and a fluid tight seal with the healthy tissue. Expansion wire 44 may be withdrawn by pulling away from the location of the aneurysm to disconnect the wire at couplings 46. Also, positioning hook 40 is retracted to its initial position beneath head 36 thereby allowing catheter 34 with wires 38 and 44 attached to be withdrawn. The outside diameter of tube 24 when fully expanded should be slightly larger than the inside diameter of the vessel being repaired. This will assure a proper tight fit which will remain fluid tight.

It will be appreciated that the method and device of the present invention may also be adapted to insert bifurcation grafts for an aneurysm involving a branched artery, such as the renal or iliac arteries. While it is preferable to use a catheter which also has angiographic capabilities, technology may soon include videodiagnostic tools to supplement or replace angiographic data. Accordingly, the invention herein described may be carried out utilizing a carrier which is a solid flexible cord or wire not intended to be used for transporting fluids. Graft 22 will normally be constructed in varying sizes to accommodate different size aneurysms. It will be appreciated, however, that so long as the graft 22 is long enough to permit anchoring into healthy tissue on either side of the damaged segment of the vessel, some leeway in the length is permissible. It will be appreciated that the specific mechanisms herein disclosed for expanding the collapsible tube 24 and for anchoring the tube to the wall of the vessel are merely illustrative and other equivalent means may be utilized without departing from the present invention.

Having thus described the invention, I claim:

1. A method of repairing a damaged segment of a blood vessel inside the body utilizing a snythetic graft characterized by being movable through the vessel in a collapsed formation utilizing an elongated flexible line, said graft being adapted to be opened up to an expanded formation wherein said graft presents a tubular opening of approximately the same size as said vessel, said method comprising the steps of:

securing said graft to an elongated flexible line adapted to be moved through said vessel;

inserting said line and said graft in its collapsed formation into said vessel at a location distal to said damaged segment;

moving said graft via said flexible line through the vessel to the area of said damaged segment;

opening said graft from its collapsed formation to its expanded formation;

permanently anchoring said graft to the wall of said vessel on either side of said damaged segment; and withdrawing said line.

2. A method as set forth in claim 1, wherein said anchoring step comprises providing a plurality of anchoring pins on said graft and piercing the wall of the vessel with said pins.

3. A method as set forth in claim 1, wherein the step of securing said graft to said line comprises securing the graft to a catheter.

* * * * *